US008588897B2

(12) United States Patent
Bigolin

(10) Patent No.: US 8,588,897 B2
(45) Date of Patent: Nov. 19, 2013

(54) DEVICE FOR DETECTING HEARTBEATS OF A PERSON USING CYCLES AND TRAINING IMPLEMENTS

(76) Inventor: Giuseppe Bigolin, Treviso (IT)

( * ) Notice: Subject to any disclaimer, the term of this patent is extended or adjusted under 35 U.S.C. 154(b) by 342 days.

(21) Appl. No.: 12/284,549

(22) Filed: Sep. 22, 2008

(65) Prior Publication Data

US 2009/0088653 A1    Apr. 2, 2009

(30) Foreign Application Priority Data

Sep. 28, 2007  (IT) .............................. MI2007A1870

(51) Int. Cl.
*A61B 5/0402* (2006.01)
(52) U.S. Cl.
USPC ........................................................ 600/520
(58) Field of Classification Search
USPC ......................................... 600/520, 521, 523
See application file for complete search history.

(56) References Cited

U.S. PATENT DOCUMENTS

| | | | | | |
|---|---|---|---|---|---|
| 3,841,316 | A | * | 10/1974 | Meyer | 600/547 |
| 4,319,581 | A | * | 3/1982 | Cutter | 600/520 |
| 4,938,475 | A | * | 7/1990 | Sargeant et al. | 482/9 |
| 5,337,753 | A | * | 8/1994 | Lekhtman | 600/519 |
| 5,430,436 | A | * | 7/1995 | Fennell | 340/7.55 |
| 5,738,104 | A | * | 4/1998 | Lo et al. | 600/521 |
| 6,018,677 | A | * | 1/2000 | Vidrine et al. | 600/520 |

* cited by examiner

*Primary Examiner* — Carl H Layno
*Assistant Examiner* — Paula J Stice
(74) *Attorney, Agent, or Firm* — Themis Law

(57) ABSTRACT

A device for detecting pulsations or heartbeats of a person using cycles in general and movable and training implements, includes a plurality of detecting electrodes operating to contact the hands of the person and operatively coupled to at least a cardiac frequency meter, the electrodes being arranged on a cycle or training implement steering control element.

12 Claims, 4 Drawing Sheets

DEVICE FOR DETECTING HEARTBEATS OF A PERSON USING CYCLES AND TRAINING IMPLEMENTS

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISK

Not Applicable

REFERENCE TO A MICROFICHE APPENDIX

Not Applicable

BACKGROUND OF THE INVENTION

1. Field of the Invention

The present invention relates to a device for detecting heartbeats of a person using cycles and training implements in general.

2. Description of Related Art

As is known, in practicing sports, the heart rate is very important for training quality and is indicative parameter of the training quality.

In fact, any sports activities would benefically affect cardiovascular blood circulation, only with a heart rate of proper value while it would be very dangerous if an excessively high heart rate was reached.

Thus, any physical training exercises must provide a well defined frequency range, with minimum and maximum frequency values depending on user parameters, such as age and an already achieved training level.

Also known is the fact that one of the most important aims of physical sports activities is the loss of weight or, in other words, consumption of excess calories.

Thus, it would also be very advantageous to hold heart rate at a proper level, to achieve the desired results.

In particular, it is important to perform any physical activities for a time sufficient to allow a person under training to only burn body fats and an amount of useful sugars as small as possible.

Accordingly, heart rate and duration of the exercise effort represent two parameters which must be accurately controlled.

At present, for measuring heart rate in sports exercises, heart rate monitoring devices including a resilient band to be worn on the thorax, and supporting two electrodes and a heartbeat detecting meter and an electronic amplifier which amplifies signals generated by the cardiac pulsating muscular mass are conventionally used, said prior devices further comprising a peak detector designed to detect a heart rate maximum for each training cycle, thereby allowing to determine single beat times, while a short range radiotransmitter emits, for each heartbeat, a corresponding pulse to a corresponding receiving device, arranged at a small distance, corresponding to a maximum of 1 m, from said transmitter and counting timeslots between two adjoining heartbeats to determine heart rate.

Such an approach, however, requires to accurately apply and locate said resilient band to correspondingly properly arrange said electrodes in a user precordial region, to in turn properly detect measurement signals, by allowing said electrodes to properly contact the user skin.

To the above the fact should be added that sweat, hairs, skin unevenness, undesired displacements of the resilient band due to user movements, and interferences of user garments against the band represent negative elements preventing an accurate measurement from being made.

Moreover, the resilient band is rather annoying and irritating for the user, thereby said band in actual practice has a very limited application.

In fact, large-breasted women generally tend not to use said resilient band since it would be very annoying.

SUMMARY OF THE INVENTION

Accordingly, the aim of the present invention is to overcome the above mentioned problems, by providing a device for detecting heartbeats and operating based on a measurement method which is at present used only for gym training activities and cannot be used on movable training implements.

Within the scope of the above mentioned aim, a main object of the invention is to provide such a device adapted to generate accurate signals truly corresponding to a user heartbeat pattern, thereby allowing heartbeats to be easily monitored.

Another object of the present invention is to provide such a device which, owing to its specifically designed construction, is very reliable and safe in operation.

Another object of the present invention is to provide such a device which can be easily made and which, moreover, is very competitive from a mere economic standpoint.

According to one aspect of the present invention, the above mentioned aim and objects, as well as yet other objects, which will become more apparent hereinafter, are achieved by a device for detecting heartbeats on a cycle in general and freely movable physical training implement, characterized in that said device comprises a plurality of electrodes for contacting the user hands and operatively coupled to at least a heart rate meter, said electrodes being arranged on a steering control element of the cycle or training implement.

BRIEF DESCRIPTION OF THE DRAWINGS

Further characteristics and advantages of the present invention will become more apparent hereinafter from the following detailed disclosure of a preferred, though not exclusive, embodiment of the device for detecting heartbeats of a person using cycles and training implements in general, which is illustrated, by way of an indicative, but not limitative example, in the accompanying drawings, where.

DESCRIPTION OF THE PREFERRED EMBODIMENTS

With reference to the number references of the above mentioned figures, the device for detecting heartbeats of a person using cycles and training implements in general, according to the present invention, comprises a handlebar 1 or other suitable steering control means, thereon the subject device is applied, and including two handles 2a and 2b respectively arranged at opposite end portions thereof.

Said handles could also be directly arranged on the handlebar 1 or applied on an already existing exercising implement.

Figure 1:
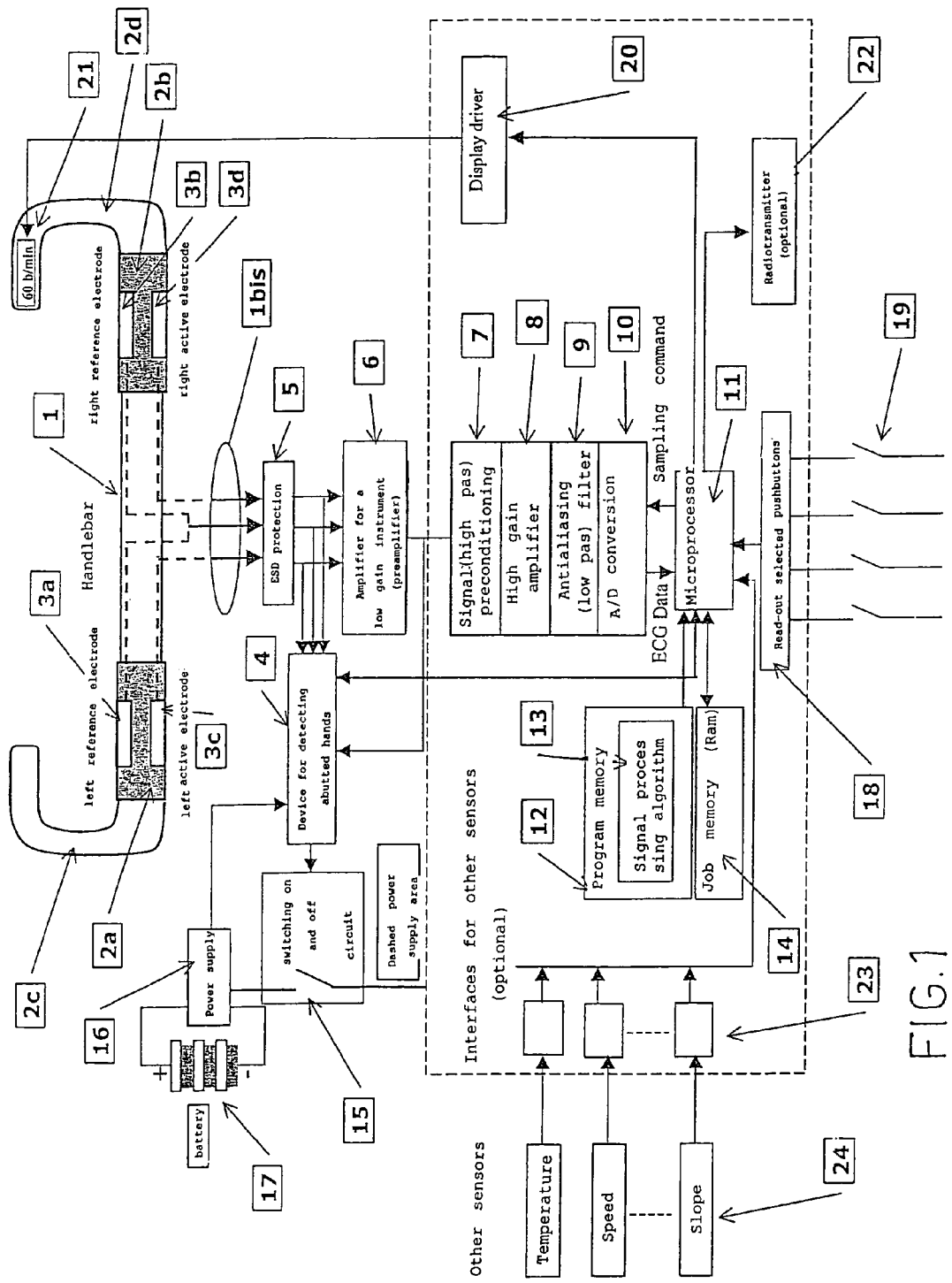
FIG. 1 is a block diagram of the device according to the invention.
Figure 2:
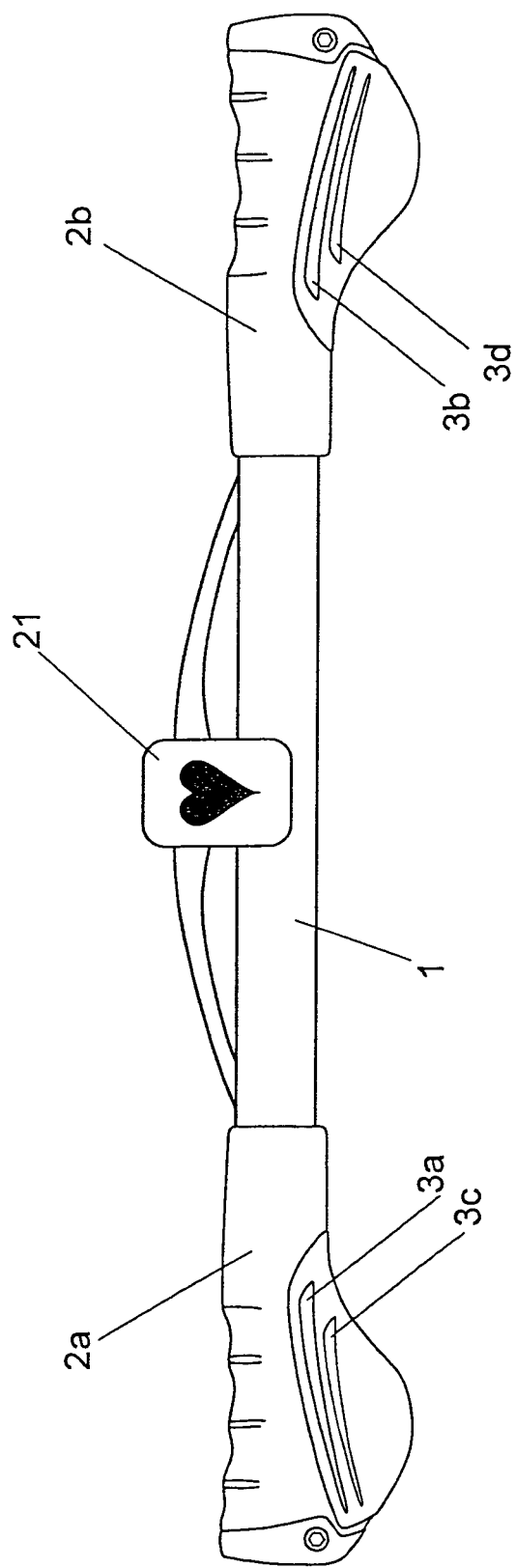
FIG. 2 schematically shows a handlebar including a plurality of measurement electrodes.
Figure 3:
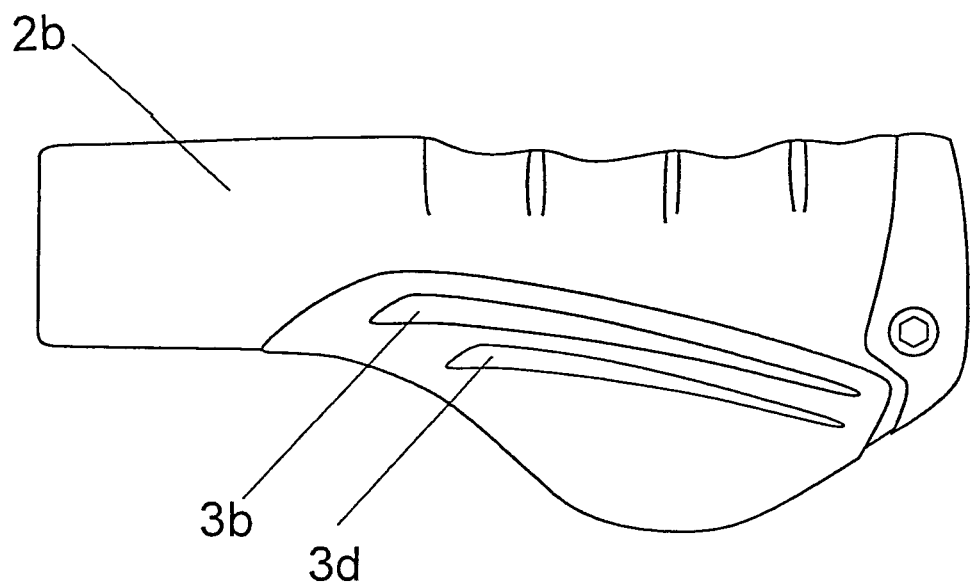
FIGS. 3 and 4 schematically show a handle, for example a right-side handle, as seen from the top and bottom faces thereof.
Figure 3:
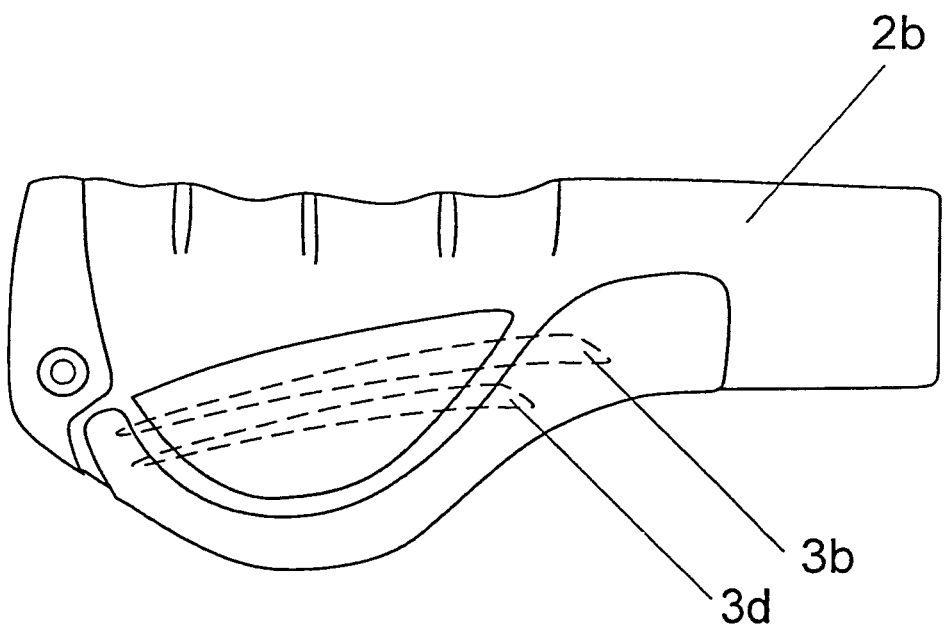
Figure 4:
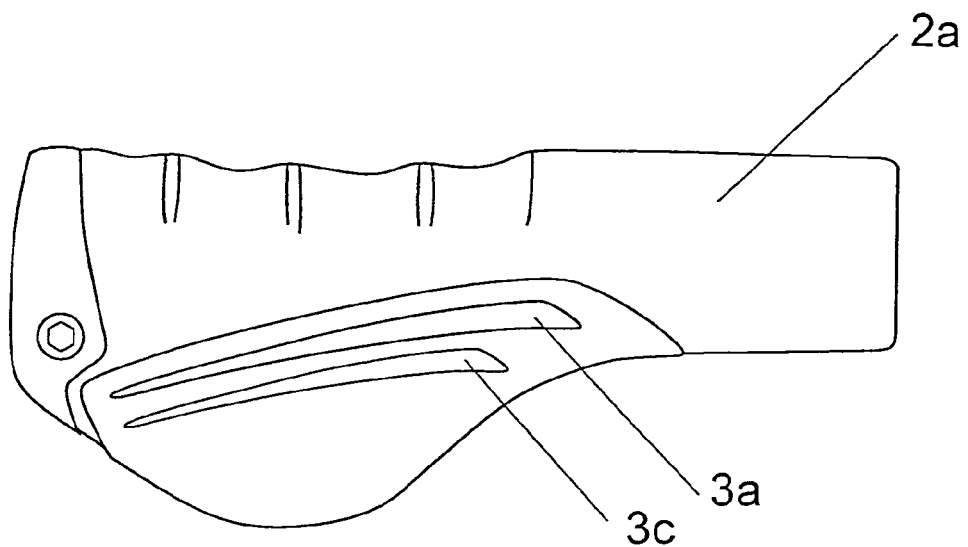
Figure 4:
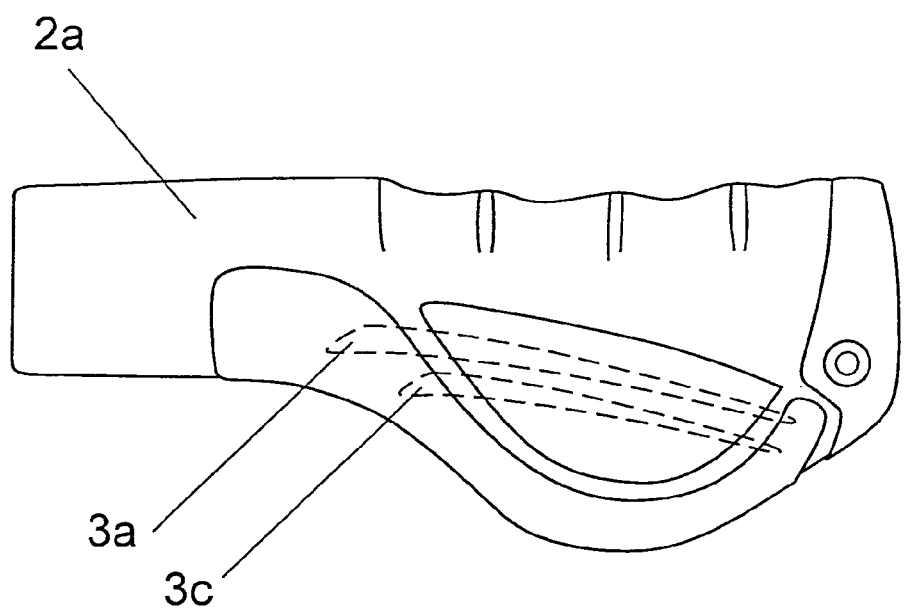

Advantageously, in the embodiment shown in FIG. 1, said handles are coupled to two hand abutment elements 2c and 2d, designed for abutting there against the hands of a user, and provide a gripping and bearing place for said hands.

Moreover, in the preferred embodiment of the device, one of said handles further comprises a display 21 allowing one to monitor the heart rate and other useful data.

Said handles comprise a plurality of electrodes allowing the user skin to be electrically contacted by specifically designed circuits adapted to pick up, amplify, and process the cardiac signal at the user hands.

The preferred embodiment, in particular, comprises top electrodes, respectively a left and a right electrode 3a and 3b, providing a reference electrode assembly, and bottom left and right electrodes, respectively indicated by 3c and 3d, forming the active electrode assembly.

Said electrodes are made either of a conductive rubber or a conductive plastic material, co-molded on a metal base, preferably a stainless steel base.

The two reference electrodes are electrically coupled to one another by wires indicated by 1 bis, allowing said electrodes to be coupled, as it will become more apparent hereinafter, to an amplifying section, and also operating to minimize noises susceptible to greatly deteriorate the electrocardiographic signals.

More specifically, to each said electrodes are coupled either one or more wiring patterns, including insulated electric wire elements, passing through the hollow inside of the handlebar tube.

Thus, the measurement circuits are suitably electrically coupled.

The input stage of said measuring circuits are provided with electrostatic protecting devices (ESD), generally indicated as 5, to avoid breaking of the stage or measurement errors when an electric discharge occurs as a consequence of electrostatic charging caused by friction in particular when the user wears garments of synthetic material, insulated shoes and the like.

The device further comprises a preamplifier 6 and a pre-processing unit 7 which, through suitable filters, remove noise sources from the signal.

In particular, the above components are designed to eliminate a low frequency biasing component formed, because of electrochemical effects, at the skin and electrode contact points and which, in general, has a level much greater than that of the useful signal and would tend to saturate the following amplifying stages, thus preventing accurate measurements from being carried out.

The invention provides moreover to use an unbalancing circuit to be connected to the input of the amplifier, and indicated by the reference number 4, operating to detect if the user has his/her hands abutting against the electrodes.

In the above arrangement, since the user, from an electric standpoint, is equivalent to a resistor having a value of some hundreds of Ohms, by unbalancing the input circuits by resistors having a much greater value, it is possible to cause the body contact to properly compensate the unbalanced condition, to recover the amplifier output to a normal value range.

This circuit is very important, since it allows to detect if the user hands are applied or not, thereby preventing a non significant signal from being processed.

Moreover, for saving power, and allowing the battery supplied device to operate for a long operating time, the preferred embodiment of the invention includes a controlled switching-off circuit 15 for automatically switching-off the device as the user does not contact by his/her hands the device.

Said switching-off circuit, in particular, after a set time, will bring the inventive device to a very low drain condition, since it is not possible to measure the frequency, for example in a non-use condition of the bicycle.

Thus, if the user does not contact by his/her hands the handlebar, the device will show, for a given period, the system clock, and then the circuit will be switched-off, with the exception of the hand abutment detecting circuit 15 and preamplifier 6, since they have a very low power drain.

The switching on and off circuit 15, in a basic embodiment thereof, comprises a solid status relay which is operatively driven to switch off the power supply 16, and which is advantageously coupled to the battery 17 preferably arranged within the handlebar 1.

Downstream of the preamplifier and pre-conditioning elements 6 and 7, is provided a further amplifying stage 8, designed for bringing the signal to a signal level compatible with required processing operations.

Moreover, the device further comprises a lowpass filtering stage 9, for eliminating harmonic components outside the useful signal band (that is above 40 Hertz, if no diagnostic application is intended), which would be very noxious, since they are generated by noise and interference phenomena caused, for example, muscular activities.

The filter cut off frequency has been selected as low as possible, to allow the signal to be reliably detected, the filter characteristic being very steep.

More specifically, a primary function of this filter is to perform a so-called antialiasing operation, for eliminating the signal sampling frequency higher harmonics in the analogic to digital conversion, required from the system microprocessor.

In fact, in the absence of said antialiasing difficulty identifiable artifacts, deriving from spurious signals having a frequency corresponding to a difference of the sampling frequency and interference noise frequency, would appear.

Thus, after amplifying and filtering, the signal is converted by a digital converter 10 and brought to a following digital processing level.

The conversion process, in particular, may be performed by available conversion methods, broadly used in the electronic field.

In such a process, the signal must have a resolution of at least 8 bit and a sampling frequency of at least 250 samples/second.

To that end, a microprocessor 11, including a suitable program memory 12 and work memory (RAM) 14, will receive and process digitized signals, transfer them to the memory means while identifying those features of the signal allowing to safely detect an electric equivalent of the heartbeat, thereby forming a digital sequence of time periods between the heartbeats, for easily measuring their frequency.

The above mentioned process is carried out based on a proper algorithm of an algorithm group 13.

In particular, the detected heart rate will be displayed on a display 21 which, in a preferred embodiment thereof, is very simple and adapted to display only numeric data and explaining icons.

Said numeric data must comprise, if possible, the heart rate or, if it is not possible in a detached-hand condition, an excess noise and so on, or as demanded by a user, the clock.

In a very simple embodiment, the above mentioned data are associated with icons representing the heart rate or the clock and, moreover, the battery charge condition.

The display 21, in the preferred embodiment, is housed in the outer end part of one of the two handles to also operate as a hand detent or gripping means for the cyclist.

In a further preferred embodiment, it is also possible to include a transmitter 22 for emitting a standard characteristic radiosignal, identical to that emitted by thorax bands, to interface the device with other existing devices connected to said thorax bands.

The disclosed electronic circuit can also comprise coupling and driving low power drain display means 20 made, for example, by the well known LCD technology.

The disclosed circuit can also comprise rate and inclination sensors 23 and 24 providing further useful information to the user, such as the caloric drain, temperature, distance and other related parameters providing an exhaustive physiologic representation of the performed training exercises.

Moreover, said circuit can also include switching or swabbing means for displaying either one or the other of the above mentioned parameters, or providing day time synchronization.

In a preferred embodiment, push buttons 18 and 19, can be mounted on the handle and suitably protected from environment noxious effects.

The above mentioned algorithm to properly measure the heart rate, starting from the sampled signal, allows to properly detect a signal portion having characteristics coherent with a typical morphology of the cardiac signal, while detecting and measuring recursive data flows coming from the user, so as to provide, for example, two typical heart rate measurements, i.e. average frequency and instantaneous frequency of the heartbeats.

The above measured raw data, furthermore, can be properly averaged, to properly define desired characteristics or interesting data for target research applications, such as a fixed time average, a movable average through the last achieved samples, or a rejection of given values, while averaging the remaining values, the movable average being related to a comparatively high number(from 10 to 20 and more)of events to prevent insignificant events from abruptly changing the frequency, and for averaging possible detection errors.

The identification of a signal, with a patient in a rest and collaborative condition or in the presence of a strong signal from the precordial region, may be substantially performed by detecting the signal peak and measuring the time period between two adjoining signal peaks, and in some cases, the identification will be followed by a suitable duration silence period for preventing possible noise or artifacts from negatively affecting the measurement.

Then, an observation window of a duration related to the measured instantaneous frequency will be opened, generally for ⅔ of the time between a heartbeat and a following heartbeat, and then said window will be closed in correspondence with the subsequent peak, in which window the heartbeat following a previously detected heartbeat will certainly fall, since, apart spurious phenomena such as extrasystoles, the heart rate cannot be physiologically change from a value included in said window.

The above method may fail if the signal is very small, great artifacts are present, as it can occur in the operating conditions of this device.

A conventional method is not however excluded, with a supported, if necessary, of a statistic method based on a sampled signal autocorrelation function, since the target searched signal would have periodic characteristics not related to masking noise or random transitory events.

Thus, an autocorrelation of following portions, of suitable length, of the target signal, will allow to properly quantify these signal portions and enhance the measurement reliability.

Accordingly, at the start of the detection cycle, it is necessary to take a signal portion having such a length as to safely contain therein at least a heartbeat.

In a normal condition, a time of 1 second is sufficient, provided that bradycardia events are excluded. Then, a series of following autocorrelations between a template and a following signal portion are performed, by causing each time the two portions of a sample to slide with respect to one another.

Thus, a likeness profile, consisting of a succession of the correlation values is obtained.

The peaks of the above mentioned succession will have a time distance from one another equal to that of the heartbeats, and are used for measuring the heartbeat frequency; since such a calculation is rather complex, a use of the first method may reduce the length of the signal portion to which the second method must be applied, so as to greatly reduce the calculation power requirement.

From the above disclosure, it should be apparent that the invention, fully achieves the intended aim and objects.

In fact, the invention provides a very practical and functional device allowing to detect heartbeats without using a conventional thorax band.

The invention as disclosed is susceptible to several modifications and variations all of which will come within the scope of the invention.

Moreover, all the constructional details can be replaced by other technical equivalent elements.

In particular, it should be apparent that the inventive device can be used on steering wheels and drive levers of cars, motorcycles, boats, airplanes and other transport means.

In practicing the invention, the used materials, provided that they are compatible to the intended application, as well as the contingent size and shapes, can be any, depending on requirements.

The invention claimed is:

1. A heartbeat detecting device to be applied to a cycle or a movable physical training implement with a handlebar, wherein the handlebar has a hollow handlebar tube and said hollow handlebar tube has opposite end portions with one handle provided at each of said opposite end portions, said heartbeat detecting device comprising:
  a reference electrode and an active electrode applicable to each of said handles; and
  a microprocessor,
  wherein the reference electrodes of both handles are electrically connected to each other with insulated electric wires, and said reference electrodes of both handles and each of said active electrodes provide an input signal to an amplifying section,
  wherein said insulated electric wires are located inside the hollow handlebar tube and are electrically isolated from the handlebar tube to transmit accurate and stable user's heart signals to the microprocessor through said amplifying section,
  wherein said amplifying section comprises,
    a pre-amplifier receiving said input signal and a pre-processing unit operatively coupled to the pre-amplifier and preconditioning the signal, said pre-amplifier and said pre-processing unit removing a low frequency biasing component from said input signal, an amplifier operatively connected to said pre-processing unit and configured to bring said input signal to a signal level compatible with downstream processing, a filtering unit operatively connected to said amplifier and configured to eliminate harmonic components disposed outside of a desired signal band, a digital converter, and said microprocessor receiving a converted signal from said digital converter and detecting an electric equivalent of a heartbeat, wherein said microprocessor comprises a program memory and a work memory, said program memory storing a set of instructions configured to provide a cardiac frequency measurement which comprises detecting a signal peak in a first measurement window, causing a silence period of duration shorter than a time between two earlier peaks, configured to prevent noise or artifacts from negatively affecting said cardiac frequency measurement, opening a second measurement window, measuring a subsequent heartbeat, and closing said second measurement window after measuring said subsequent heartbeat.

2. The device as claimed in 1, further comprising an electrostatic charge protection device receiving said input signal and feeding said input signal to said amplifying section.

3. The device as claimed in 1, wherein hand abutment elements are mounted to said handles for abutting the hand of a user there against.

4. The device as claimed in 1, wherein said device comprises a hand contact detecting circuit operatively coupled to a controlled switching off circuit.

5. The device as claimed in 4, wherein said controlled switching off circuit is connected to a power supply battery.

6. The device as claimed in 5, wherein that said power supply battery is arranged within a control element in said handlebar.

7. The device as claimed in 1, wherein said microprocessor is connected to a display.

8. The device as claimed in 7, wherein said display is arranged on the handlebar, one handle, a back mirror or a device worn by the user.

9. The device as claimed in 7, wherein coupling and driving means are provided for coupling and driving said display.

10. The device as claimed in 7, wherein a plurality of sensor means are coupled to said microprocessor.

11. The device as claimed in 7, wherein a plurality of push-buttons are operatively coupled to said microprocessor for controlling said display and device operation.

12. The device as claimed in 1, wherein coupling means are provided for coupling to a steering wheel, a control lever mounted on cars, motorcycles, boats, or airplanes.

* * * * *